United States Patent [19]
Vinopal et al.

[11] Patent Number: 5,540,920
[45] Date of Patent: Jul. 30, 1996

[54] SYNERGISTIC BIOCIDE COMPOSITION CONTAINING PYRITHIONE PLUS AN ADDITIVE

[75] Inventors: Robert T. Vinopal, Mansfield; John D. Nelson, Jr., Bethlehem; Michael W. Glynn, Darien; Robert W. Coughlin, Storrs; Robert F. Vieth, Manchester; Jon R. Geiger, West Hartford, all of Conn.

[73] Assignee: Olin Corporation, Cheshire, Conn.

[21] Appl. No.: 343,802

[22] Filed: Nov. 22, 1994

[51] Int. Cl.$^6$ .................................................. A01N 25/00
[52] U.S. Cl. ................................................................ 424/405
[58] Field of Search .............................................. 424/405

[56] References Cited

U.S. PATENT DOCUMENTS

| | | | |
|---|---|---|---|
| 2,809,971 | 10/1957 | Bernstein et al. | 260/270 |
| 3,159,640 | 12/1964 | McClure et al. | 260/294.8 |
| 4,242,336 | 12/1980 | Hasegawa et al. | 424/246 |
| 5,342,437 | 8/1994 | Gavin et al. | 106/18.33 |
| 5,354,902 | 10/1994 | Merciadez et al. | 562/601 |

FOREIGN PATENT DOCUMENTS

| | | |
|---|---|---|
| 273202 | 7/1988 | European Pat. Off. . |
| 376852 | 7/1990 | European Pat. Off. . |
| 7-157415 | of 1995 | Japan . |
| 9217184 | 1/1992 | WIPO . |
| 9412115 | 6/1994 | WIPO . |

OTHER PUBLICATIONS

CA 112:204442 1988.
CA 106:89939 1986.
Japanese Kokai 59–(1984) 98001.

*Primary Examiner*—Paul J. Killos
*Attorney, Agent, or Firm*—Dale L. Carlson

[57] ABSTRACT

Disclosed herein is an antimicrobial composition characterized by synergistic antibacterial and antifungal efficacy and comprising a pyrithione salt or pyrithione acid, and at least one compound selected from the group consisting of benzyl and lower alkyl esters of para-hydroxybenzoic acid, salts thereof, carboxylic acids, salts thereof, and combinations thereof. Also disclosed is a method of imparting antimicrobial activity to a composition comprising water or an organic solvent which comprises adding thereto an antimicrobially effective amount of the above-described antimicrobial composition.

13 Claims, No Drawings

5,540,920

1

SYNERGISTIC BIOCIDE COMPOSITION CONTAINING PYRITHIONE PLUS AN ADDITIVE

FIELD OF THE INVENTION

This invention relates generally to synergistic biocide compositions, and, more specifically, to a composition comprising pyrithione or a pyrithione salt, and a benzyl or lower alkyl ester of para-hydroxybenzoic acid or a salt thereof, or a carboxylic acid or a salt thereof, or combination thereof.

BACKGROUND OF THE INVENTION

Biocides provide antimicrobial protection for industrial, personal care, medical and other products and materials. Typically, the biocide has a somewhat limited range with respect to the specific microorganisms it will kill, has some toxicity, and presents some environmental hazard, or a combination of these drawbacks. Thus, it would be useful to find a means to enhance biocidal activity, or extend the range of antimicrobial effectiveness of biocides, without increasing toxicity or the degree of environmental hazard of these compounds.

Certain combinations of pyrithione with other additives to provide a preservative, antibacterial or antifungal efficacy are known in the art. For example, Japanese Kokai 59-(1984)98001 discloses a cut flower preservative comprising pyrithione or a salt thereof, an aliphatic carboxylic acid, and a saccharide. U.S. Pat. No. 4,242,336 discloses an antibacterial and antifungal composition comprising (a) at least one member selected from the group consisting of dehydroacetic acid, sorbic acid and their alkali metal salts and (B) at least one member selected from the group consisting of alkyl(aminoethyl)-glycines having C8 to C16 alkyl groups and their salts, 2-pyridine-thiol 1-oxide (i.e., pyrithione) and its salts, and tetrahydro-3,5-dimethyl-2H-1, 3,5-thiadiazine-2-thione. However, these references do not disclose the basis for the efficacy of these disclosed combinations, nor do they suggest other antimicrobial combinations. Furthermore, the sorbic acid disclosed in the '336 patent is subject to chemical instability problems, necessitating the use of a stabilizer to inhibit oxidation, such as manganous ion, as disclosed in U.S. Pat. No. 5,354,902.

New combinations of pyrithione with other additives, exhibiting synergistic efficacy over a wide range of use concentrations, without the need for (and preferably in the absence of) any oxidative inhibition stabilizer, would be highly desired by the biocides community, particularly if such compositions also exhibit low toxicity against mammals. The present invention provides several of such combinations.

SUMMARY OF THE INVENTION

In one aspect, the present invention relates to an antimicrobial composition characterized by synergistic antibacterial and antifungal efficacy and comprising pyrithione acid or a pyrithione salt, or a combination thereof, and at least one compound selected from the group consisting of benzyl and lower alkyl esters of para-hydroxybenzoic acid, salts thereof, carboxylic acids, salts thereof, and combinations thereof, said carboxylic acid being selected from the group consisting of gallic, malic, tartaric, undecylenic, salicylic, p-aminobenzoic, benzoic, propionic, lactic, citric acids and combinations thereof. The antimicrobial composition is preferably free of an oxidative inhibition stabilizer additive.

2

In another aspect, the present invention relates to a method of imparting antimicrobial activity to a composition comprising water or an organic solvent which comprises adding thereto an antimicrobially effective amount of the above-described antimicrobial composition.

In yet another aspect, the present invention relates to a method of coating a substrate to provide an antimicrobially effective coating on the substrate which comprises contacting the substrate with a coating composition comprising the above-described antimicrobial composition.

In still another aspect, the present invention relates to a coated substrate comprising a substrate together with a coating on said substrate, said coating being produced by (a) contacting the substrate with a coating composition comprising the above-described antimicrobial composition, and (b) drying said coating composition on said substrate to produce said coated substrate.

In yet another aspect, the present invention relates to a paint comprising:

(a) a base medium comprising water or a resin selected from the group consisting of vinyl, alkyd, epoxy, acrylic, polyurethane and polyester resins, and combinations thereof, and (b) the above-described antimicrobial composition. The antimicrobial composition is employed in the paint in an amount at least sufficient to act as an "in-can preservative" during storage prior to use. Alternatively, the antimicrobial composition can be employed in an amount sufficient to provide antimicrobial efficacy for the paint when dried on a substrate.

In still another aspect, the present invention relates to a soap, shampoo or skin care medicament comprising a suitable carrier and the above-described antimicrobial composition.

In still another aspect, the present invention relates to a metalworking fluid containing water or an organic base fluid, and the above-described antimicrobial composition. Another aspect of the invention relates to the above-described metalworking fluid which additionally comprises a component selected from the group consisting of corrosion inhibitors, surfactants, and combinations thereof.

In yet another aspect, the present invention relates to a composition comprising a plastic or a woven or non-woven fiber which comprises, in combination, a plastic or a fiber and the above-described antimicrobial composition.

These and other aspects will become apparent upon reading the following detailed description of the invention.

DETAILED DESCRIPTION OF THE INVENTION

It has now been surprisingly found in accordance with the present invention that the combination of pyrithione acid, or a salt thereof, with a select carboxylic acid, or salt thereof, with the benzyl and lower alkyl ester of para-hydroxybenzoic acid (also referred to herein as "paraben"), or a salt thereof, or a combination thereof, provides synergistic antimicrobial effectiveness as an antifungal and antibacterial composition. An increased understanding of the mode of action in accordance with the present invention provides a better understanding of antimicrobial enhancing additives for use in combination with pyrithione. Without wishing to be bound by any particular theory, it is believed by the present inventors that the synergistic efficacy associated with the compositions of the present invention is attributable to the relative toxicity of the carboxylic acid or paraben co-biocide to the microorganism being attacked in the presence of the pyrithione biocide in view of the present inventors understanding of the antimicrobial mode of action of pyrithione. The pyrithione acts to collapse the proton motive force that provides the energy link for microbial metabolism, by catalyzing the electroneutral exchange of hydrogen ions and potassium ions across microbial cell membranes.

In light of the above-described mode of action, the present inventors have discovered that select classes of compounds provide synergistic antimicrobial effectiveness in combination with pyrithione, namely specific carboxylic acids, or salts thereof, or the benzyl and lower alkyl esters of parahydroxybenzoic acid (also referred to herein as "paraben"), or a salt thereof, or combinations of these compounds. The term "paraben" is also intended to encompass organic solutions, such as ethanolic solutions of methylparaben ("MP"), propylparaben ("PP"), or butylparaben ("BP").

As used herein, the term "synergistic antimicrobial effectiveness" means that the composition exhibits greater antimicrobial activity than the additive amounts of activity provided when each component of the combination is employed alone. The composition exhibits synergistic antimicrobial activity with respect to the growth of microorganisms, notably bacteria and fungi. The antimicrobial activity is provided during use of the composition, for example, in an aqueous industrial functional fluid composition, such as a metalworking fluid, lubricant, or diagnostic reagent for immunological testing, in order to provide biocidal protection against microbes such as bacteria and fungi during use of the fluid.

The pyrithione used in the process and composition of this invention is preferably a pyrithione salt, such as sodium pyrithione, zinc pyrithione, chitosan pyrithione, magnesium disulfide pyrithione, copper pyrithione, and the like, although pyrithione acid can be used if desired. More preferable pyrithione salts include sodium pyrithione, copper pyrithione, and zinc pyrithione, most preferably sodium pyrithione.

The sodium pyrithione useful in the present invention is a well-known commercial product that is commonly made by reacting 2-chloropyridine-N-oxide with NaSH and NaOH, as illustrated by the disclosures of U.S. Pat. No. 3,159,640.

Zinc pyrithione may be made by reacting 1-hydroxy-2-pyridinethione (i.e., pyrithione acid) or a soluble salt thereof with a zinc salt (e.g., $ZnSO_4$) to form a zinc pyrithione precipitate, as illustrated by the disclosures of U.S. Pat. No. 2,809,971.

In use, the antimicrobial composition of the present invention preferably contains a weight ratio of carboxylic acid, or salt thereof, to pyrithione of between about 1:1 and about 10,000:1, more preferably between about 1:1 and about 6,000:1. If paraben or a salt thereof is employed in the antimicrobial composition, then it is preferred that the weight ratio of the paraben compound to the pyrithione be between about 1:10 and about 10,000:1, more preferably between 1:6 and 156:1.

The antimicrobial compositions of the present invention are suitable for a variety of uses, such as, for example in soap, shampoo, skin care medicaments, metalworking fluids, paint, or incorporated into or onto plastic or a woven or non-woven fibers.

One significant use application for the antimicrobial compositions of the present invention is in functional fluids, such as metalworking fluids. These functional fluids are typically supplied as an aqueous concentrate containing the antimicrobial composition and the other components of the functional fluid. In the aqueous concentrate, a sufficient amount of the antimicrobial composition is provided such that the "working" functional fluid will contain a biocidally effective amount thereof. In order to satisfy this requirement, the concentrate for a metalworking fluid, for example, preferably contains a total amount of up to about 2.5 weight percent of the antimicrobial composition, based upon the weight of the metalworking fluid, in order to provide a preferred amount of at least about 1250 ppm of the antimicrobial composition in the "working" fluid, based upon a dilution rate of the concentrate to the "working" fluid of between about 1:10 and about 1:100. Other functional fluids, such as cosmetics, are often formulated directly (without the need for a concentrate) and can contain up to 5000 ppm, or more, of the antimicrobial composition.

The antimicrobial compositions of the present invention are also useful in paints, including indoor and outdoor household paints, industrial and commercial paints. Particularly advantageous results are obtained when the compositions of the present invention are utilized in conjunction with marine paints for use, for example, on ship's hulls. In addition, the antimicrobial compositions provide desirable results in exterior paints of the latex and alkyd types. The antimicrobial composition is also useful as an "in-can" preservative during storage and prior to use of the paint.

Typically a paint composition will contain a resin, a pigment, and various optional additives such as thickening agent(s), wetting agents and the like, as is well known in the art. The resin is preferably selected from the group consisting of vinyl, alkyd, epoxy, acrylic, polyurethane and polyester resins, and combinations of thereof. The resin is preferably employed in an amount of between about 20% and about 80% based upon the weight of the paint or paint base.

In addition, the paint composition of the present invention optionally additionally contains optional additives which have a favorable influence on the viscosity, the wetting power and the dispersibility, as well as on the stability to freezing and electrolytes and on the foaming properties. If a marine paint is being fabricated, the paint preferably contains a swelling agent to cause the paint to gradually "slough off" in its marine environment, thereby causing renewed biocidal efficacy of newly exposed biocide at the surface of the paint in contact with the water medium of the marine environment. Illustrative swelling agents are naturally occurring or synthetic clays, such as kaolin, montomorillonite, and bentonite), clay mica (muscovite), and chlorite (hectonite), and the like. In addition to clays other swelling agents, including natural or synthetic polymers, such as that commercially available as POLYMERGEL, have been found to be useful in the compositions of the present invention to provide the desired "sloughing off" effect. Swelling agents can be used singly or in combination. The total amount of optional additives is preferably no greater than 20% by weight, more preferably between about 1% and about 5% by weight, based upon the total weight of the paint composition.

Illustrative, thickening agents include cellulose 30 derivatives, for example methyl, hydroxyethyl, hydroxypropyl and carboxymethyl cellulose, poly(vinyl alcohol), poly (vinylpyrolidone), poly(ethyleneglycol), salts of poly(acrylic acid) and salts of acrylic acid/acrylamide copolymers.

Suitable wetting and dispersing agents include sodium polyphosphate, salts of low molecular weight poly(acrylic acid), salts of poly(ethane sulfonic acid), salts of poly (vinyl phosphonic acid), salts of poly(maleic acid) and salts of copolymers of maleic acid with ethylene, 1 olefins 3 to 18 carbon atoms and/or styrene.

In order to increase the stability to freezing and electrolytes there may be added to the paint composition various monomer 1.2-diols for example glycol, propylene glycol (1.2) and butylene glycol 1.2) or polymers thereof, or ethoxylated compounds. For example reaction products of ethylene oxide with long-chain alkanols, amines, alkyd phenols, poly(propyleneglycol), or poly(butylene glycol), or a combination thereof, or the like.

The minimum temperature of film formation (white point) of the paint composition may be reduced by adding solvents, such as ethylene glycol, butyl glycol, ethyl glycol acetate, ethyl diglycol acetate, butyl diglycol acetate, benzene or alkylated aromatic hydrocarbons. As defoaming agents there are suitable for example poly(propylene glycol) and polysiloxanes. Optionally other biocides can additionally be incorporated into the paint formulations of the present invention. Useful optional solvents include methylisobutylketone (herein referred to as "MIBK"), xylene, ethyl benzene, methanol, and combinations thereof.

The paint composition of the present invention may be used as a paint for natural or synthetic materials, for example wood, paper, metals, textiles and plastics. It is particularly suitable as an outdoor paint, and is excellent for use as a marine paint.

The compositions of the present invention are useful, in any of the variety of applications described herein, as disinfectants and preservatives, in a liquid or spreadable solid form, alone or in combination with an inert carrier such as water, liquid hydrocarbons, ethanol, isopropanol, or the like. They can be employed using conventional procedures to control bacteria and fungi in various substrates, and can be applied to bacterial or fungal organisms or their substrates in an antimicrobial amount by conventional procedures such as spraying, dipping, drenching impregnation, and the like.

The invention is further illustrated by the following Examples. Unless otherwise stated, the "parts" and "%" are "parts by weight" and "percent by weight", respectively.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

EXAMPLE 1

MIC Data on Pyrithione Plus Parabens or Carboxylic Acid

Interactions of sodium pyrithione with other compounds were assessed using a modification of the "checkerboard" MIC ("minimum inhibitory concentration") procedure described by Dougherty, P. F., et al. 1977. Microdilution Transfer Plate Technique for Determining In Vitro Synergy of Antimicrobial Agents. Antimicrobial Agents and Chemotherapy. 11:225–228. This procedure facilitates the measurement of the effects of a large number mixtures of different ratios of biocides. Stock solutions of pyrithiones in Tryptic Soy Broth (TSB) were diluted in TSB in microliter plates, and the test compounds were diluted in tubes of TSB. Aliquots of each dilution of test compound were added to the wells containing pyrithione dilutions and undosed TSB as a control, leaving rows of unmixed pyrithione or test compound for the determination of MIC's of pure pyrithione or test compounds. An equal volume of test culture containing $10^6$ bacteria/ml or $10^5$ fungal spores/ml suspended in TSB was added to each well, and the plates were incubated at 28° C. The lowest concentration resulting in growth inhibition (MIC) was determined. The Fractional Inhibitory Concentration (FIC), ie. ratio of the MIC of a biocide in a mixture to that of the pure substance, was determined, and the sum of the FIC's ("FIC Index") for each mixture was calculated. Each type of interaction was quantified and categorized according to the following: synergistic if <1; additive if =1; antagonistic if >1.

Mixtures containing varying proportions of pyrithione and organic acids or methyl paraben synergistically inhibited a bacterium (*Pseudomonas aeruginosa*) and a fungus (*Aspergillus niger*), for which the MIC data are given in Tables 1 and 2, respectively.

TABLE 1

Synergistic Antibacterial Effects of Sodium Pyrithione (NPT) Mixtures
MIC of Mixture (ppm)[a]

| Test Compound | Test Compound ("TC") | NPT, ppm | Ratio (TC/NPT) | FIC Index[b] |
|---|---|---|---|---|
| none | 0 | 128 | — | — |
| salicylic acid | 6250 | 0 | — | — |
| " | 3125 | 8 | 391/1 | 0.56 |
| " | 1563 | 32 | 49/1 | 0.50 |
| " | 781 | 32 | 24/1 | 0.38 |
| " | 391 | 64 | 6/1 | 0.56 |
| p-aminobenzoic acid | 6250 | 0 | — | — |
| " | 3125 | 16 | 195/1 | 0.63 |
| " | 1563 | 32 | 49/1 | 0.50 |
| " | 781 | 64 | 12/1 | 0.63 |
| benzoic acid | 6250 | 0 | — | — |
| " | 3125 | 4 | 781/1 | 0.53 |
| " | 1563 | 16 | 98/1 | 0.38 |
| " | 781 | 32 | 24/1 | 0.38 |
| " | 391 | 32 | 12/1 | 0.31 |
| propionic acid | 3125 | 0 | — | — |
| " | 1563 | 2 | 781/1 | 0.52 |
| " | 781 | 64 | 12/1 | 0.75 |
| lactic acid | 22,225 | 0 | — | — |
| " | 11,113 | 16 | 695/1 | 0.63 |
| " | 5560 | 32 | 174/1 | 0.50 |
| " | 2780 | 64 | 43/1 | 0.62 |
| citric acid | >25,000 | 0 | — | — |
| " | 12,500 | 8 | >1563/1 | <0.56 |
| " | 6250 | 16 | >391/1 | <0.38 |
| " | 3125 | 16 | >195/1 | <0.25 |
| " | 1563 | 32 | >49/1 | <0.31 |
| " | 781 | 64 | >12/1 | <0.53 |
| " | 391 | 64 | >6/1 | <0.52 |
| methyl ester of p-hydroxybenzoate | 2500 | 0 | — | — |
| methyl ester of p-hydroxybenzoate | 625 | 16 | 39/1 | 0.38 |
| methyl ester of p-hydroxybenzoate | 313 | 32 | 10/1 | 0.38 |
| methyl ester of p-hydroxybenzoate | 156 | 32 | 5/1 | 0.31 |
| methyl ester of p-hydroxybenzoate | 78 | 32 | 2/1 | 0.28 |
| methyl ester of p-hydroxybenzoate | 39 | 64 | 1/2 | 0.52 |
| methyl ester of p-hydroxybenzoate | 20 | 64 | 1/3 | 0.51 |
| methyl ester of p-hydroxybenzoate | 10 | 64 | 1/6 | 0.50 |

TABLE 1-continued

Synergistic Antibacterial Effects
of Sodium Pyrithione (NPT) Mixtures
MIC of Mixture (ppm)[a]

| Test Compound | Test Compound ("TC") | NPT, ppm | Ratio (TC/NPT) | FIC Index[b] |
|---|---|---|---|---|
| none | 0 | 64 | — | — |
| sorbic acid | 4096 | 0 | — | — |
| " | 2048 | 16 | 128/1 | 0.75 |
| " | 1024 | 32 | 32/1 | 0.75 |
| " | 512 | 32 | 16/1 | 0.63 |
| " | 256 | 32 | 8/1 | 0.56 |

[a]Minimum Inhibitory Concentrations (MIC's) were determined against *Pseudomonas aeruginosa* NCIMB strain 6749. NPT and inocula of bacterial cells were added to Tryptic Soy Broth (TSB) adjusted to pH 5.8. Test compounds were dissolved in TSB, and the resulting solutions were adjusted to pH 5.8 and filter-sterilized. The mixtures were diluted in TSB (pH 5.8) and incubated at 28° C. for 4 to 6 days.
[b]Fractional Inhibitory Concentration Index: additive effect if = 1; synergistic if <1; antagonistic if >1.

TABLE 2

Synergistic Antifungal Effects
of Sodium Pyrithione (NPT) Mixtures
MIC of Mixture (ppm)[a]

| Test Compound | Test Compound ("TC") | NPT, ppm | Ratio (TC/NPT) | FIC Index[b] |
|---|---|---|---|---|
| none | 0 | 32 | — | — |
| salicylic acid | 6250 | 0 | — | — |
| " | 3125 | 1 | 3125/1 | 0.53 |
| " | 1563 | 16 | 98/1 | 0.75 |
| sorbic acid | 1250 | 0 | — | — |
| " | 625 | 8 | 78/1 | 0.75 |
| " | 313 | 8 | 39/1 | 0.50 |
| benzoic acid | 1500 | 0 | — | — |
| " | 750 | 4 | 188/1 | 0.75 |
| propionic acid | 3125 | 0 | — | — |
| " | 1563 | 0.25 | 6252/1 | 0.51 |
| " | 781 | 4 | 195/1 | 0.38 |
| none | 0 | 64 | — | — |
| methyl ester of p-hydroxybenzoate | 1250 | 0 | — | — |
| methyl ester of p-hydroxybenzoate | 625 | 4 | 156/1 | 0.56 |
| methyl ester of p-hydroxybenzoate | 313 | 16 | 20/1 | 0.50 |
| methyl ester of p-hydroxybenzoate | 156 | 16 | 10/1 | 0.38 |
| methyl ester of p-hydroxybenzoate | 78 | 16 | 5/1 | 0.31 |
| methyl ester of p-hydroxybenzoate | 39 | 16 | 2/1 | 0.28 |
| methyl ester of p-hydroxybenzoate | 20 | 32 | 1/2 | 0.52 |
| methyl ester of p-hydroxybenzoate | 10 | 32 | 1/3 | 0.50 |

[a]Minimum Inhibitory Concentrations (MIC's) were determined against an environmental isolate of the fungus, *Aspergillus niger*. NPT and inocula of fungal spores were added to Tryptic Soy Broth (TSB) adjusted to pH 4.5. Test compounds were dissolved in TSB, and the resulting solutions were adjusted to pH 4.5 and filter sterilized. The mixtures were diluted in TSB (pH 4.5) and incubated at 28° C. for 12 to 13 days.
[b]Fractional Inhibitory Concentration Index: additive effect if = 1; synergistic if <1; antagonistic if >1.

EXAMPLE 2

Metalworking Fluid Containing Pyrithione and Paraben

The efficacy of a sodium pyrithione-methyl paraben mixture as a preservative was measured in an oil in water emulsion metalworking fluid challenged with a mixture of bacteria and fungi. A 5% aqueous emulsion of concentrated MWF, consisting of mineral oil (83.5%), sulfonated hydrocarbon (10.7%), oleic acid (1.0%), triethanolamine (0.8%), methyl tallowate (3.0%), and propylene glycol ether (1.0%) was dosed with 125 ppm of sodium pyrithione and 1000 ppm of methyl paraben and dispersed into Erlenmeyer flasks. A challenge level of $10^7$ cells of bacteria and $10^5$ fungal spores per ml of emulsion was initiated by adding a suspension of seven bacteria and two fungi originally isolated from contaminated MWF's (*Pseudomonas rubescens* NCIMB 12202, *Pseudomonas stutzeri* sp., *Pseudomonas fluorescens* NCIMB 12201, *Pseudomonas aeruginosa* NCIMB 6749, *Pseudomonas oleovorans* NCIMB 6576, *Alcaligenes faecalis* sp., *Citrobacter freundii* NCIMB 12203, *Fusarium* sp. and *Cephalosporium* sp.). The fluids were agitated continuously on a rotary shaker and sampled periodically for viable bacteria on Tryptic Soy Agar and for fungi on Tryptic Soy Agar supplemented with 100 mg gentamicin sulfate per liter. After two weeks, a pronounced synergistic inhibition of bacteria and fungi was observed in the pyrithione-methyl paraben fluid relative to the untreated control, as shown by the data presented in Table 3 below. Inhibition was also established when the fluids were challenged a second time (see Table 3).

TABLE 3

Efficacy of Sodium Pyrithione/Methyl Paraben
Mixture in an Oil in Water Emulsion*

| Treatment | Time (days) | Average Viable Count/ml | |
|---|---|---|---|
| | | Bacteria | Fungi |
| blank | 7 | 20,700,000 | 150,000 |
| NPT (125 ppm) | 7 | 12,400,000 | 134,000 |
| MP (1,000 ppm) | 7 | 5,930,000 | 44,000 |
| NPT (125) + MP (1000) | 7 | >1,000,000 | 27,000 |
| blank | 12 | 25,900,000 | 94,000 |
| NPT (125 ppm) | 12 | 8,190,000 | 44,000 |
| MP (1,000 ppm) | 12 | 442,000 | 53,000 |
| NPT (125) + MP (1000) | 12 | <260 | 100 |
| | 14 | Re-challenge | |
| blank | 19 | 39,500,000 | 152,000 |
| NPT (125 ppm) | 19 | 25,200,000 | 106,000 |
| MP (1000 ppm) | 19 | 4,160,000 | 74,000 |
| NPT (125) + MP (1000) | 19 | 25,700 | 19,200 |
| blank | 27 | 29,500,000 | 270,000 |
| NPT (125 ppm) | 27 | 16,500,000 | 50,000 |
| MP (1000 ppm) | 27 | 375,000 | 50,000 |
| NPT (125) + MP (1000) | 27 | <26,000 | <1000 |

*5% aqueous emulsion of metalworking fluid concentrate treated with sodium pyrithione (NPT) and methyl paraben (MP).

EXAMPLE 3

Latex Paint Containing Sodium Pyrithione and Paraben

The efficacy of sodium pyrithione plus paraben mixtures was measured in a latex paint artificially contaminated with *Pseudomonas aeruginosa*. A representative vinylacrylic flat latex house paint formulation (consisting of water (30%), ethylene glycol (2.20%), anionic dispersant (0.58%), defoamer (0.33%), hydroxyethyl cellulose (0.25%), potassium tripolyphosphate (0.08%), silicate filler (20.60%), titanium dioxide (18.50%), propylene glycol (2.80%), attapulgite clay (0.49%), alcohol ethoxylate (0.21%), latex (30.20%), and an alcohol ester coalescent (0.74%)) was diluted in sterile water to 10% to simulate a factory rinse water-condensation situation and inoculated with a broth culture of *Pseudomonas aeruginosa* ATCC 10145. Growth was monitored by culturing the paint solution on slants of Tryptone Glucose Extract Agar (TGEA, Difco) incubated at 29° C. for 5 days. Ten grams of uncontaminated 10% paint were weighed into glass vials and amended with aqueous solutions of sodium pyrithione (referred to herein as "SP") or ethanolic solutions of methylparaben ("MP"), propylparaben ("PP"), or butylparaben ("BP"). Blanks containing an equivalent amount of ethanol (50 microliters) were included. Each vial was inoculated with 1% by volume of contaminated dilute paint ($2.0 \times 10^6$ CFU/ml). Survival of the contaminant was assessed periodically by subculturing the samples to slants of TGEA as before. After 32 days, the paint samples were re-challenged with 1% by volume of the dilute contaminated paint.

The results provided in Table 4 show that mixtures of 500 ppm of pyrithione and 1000 ppm of paraben were more antimicrobially effective after one week than either preservative alone. In addition the data in Table 4 indicate that methyl- and propylparabens were relatively more effective synergists than butylparaben. After re-challenge, a combination of 1000 ppm methylparaben and between 500 and 1000 ppm sodium pyrithione was the most effective synergistic combination in this test.

In a second experiment, for which the results are shown in Table 5, undiluted similarly contaminated paint was amended with methylparaben and sodium pyrithione in various ratios and periodically assayed for growth as in the first experiment. The samples were rechallenged with 2% by volume of contaminated paint ($8.7 \times 10^6$ CFU/ml) on the 21st and 69th days. Mixtures of 500 pppm sodium pyrithione plus 500 or 1000 ppm methylparaben proved to be effective throughout much of the test, but 500 ppm sodium pyrithione plus 1000 ppm methylparaben provided maximum antimicrobial effectiveness in this test. The results are given in Table 5.

In Tables 4 and 5 "−" denotes no surviving microbial growth of the test organism, whereas "+" denotes very little survival, "++ and +++" denote minimal microbial survival, and "++++" and "+++++" denote significant microbial survival.

TABLE 4

IN-CAN PAINT PRESERVATIVE EFFICACY

| DAY | GROWTH (TGEA Subculture) Preservative (ppm, w/w) | | | | | |
|---|---|---|---|---|---|---|
| | blank | SP 500 | SP 1000 | MP 1000 | PP 1000 | BP 1000 |
| 1 | +++++ | ++++ | +++ | +++++ | +++++ | +++++ |
| 8 | +++++ | +++ | ++ | +++++ | +++++ | +++++ |
| 15 | +++++ | ++++ | + | +++++ | +++++ | +++++ |
| 25 | +++++ | +++++ | − | +++++ | +++++ | +++++ |
| 32 | | | Re-challenge | | | |
| 39 | +++++ | +++++ | +++ | +++++ | +++++ | +++++ |

| | SP 500 + MP | SP 500 + PP | SP 500 + BP | SP 1000 + MP | SP 1000 + PP | SP 1000 + BP |
|---|---|---|---|---|---|---|
| 1 | ++++ | ++++ | ++++ | +++ | ++++ | ++++ |
| 8 | + | ++ | +++ | + | ++ | ++ |
| 15 | − | − | ++ | − | − | + |
| 25 | − | − | + | − | − | − |
| 32 | | | Re-challenge | | | |
| 39 | ++ | ++++ | ++++ + | + | +++ | +++ |

TABLE 5

EFFICACY OF PYRITHIONE + METHYLPARABEN MIXTURES

| DAY | GROWTH (TGEA Subculture) Preservatives (ppm, w/w) | | | | | | | | |
|---|---|---|---|---|---|---|---|---|---|
| | blank | SP 250 ppm | SP 500 ppm | MP 500 ppm | MP 1000 ppm | SP 250 ppm + MP 500 ppm | SP 500 ppm + MP 500 ppm | SP 250 ppm + MP 1000 ppm | SP 500 ppm + MP 1000 ppm |
| 7 | +++++ | + | + | +++++ | +++++ | ++++ | ++ | +++ | + |
| 14 | +++++ | − | − | +++++ | +++++ | − | − | − | − |
| 21 | +++++ | − | − | +++++ | +++++ | − | − | − | − |
| | | | | | Re-challenge | | | | |
| 28 | +++++ | +++++ | − | +++++ | +++++ | ++ | + | + | − |
| 35 | +++++ | +++++ | − | +++++ | +++++ | − | − | − | − |
| 42 | +++++ | +++++ | − | +++++ | +++++ | + | − | − | − |
| 49 | +++++ | +++++ | − | +++++ | +++++ | +++ | − | − | − |
| 56 | +++++ | +++++ | − | +++++ | +++++ | − | − | − | − |
| 63 | +++++ | +++++ | − | +++++ | +++++ | +/− | − | − | − |
| 69 | +++++ | +++++ | − | +++++ | +++++ | +/− | − | − | − |

TABLE 5-continued

EFFICACY OF PYRITHIONE + METHYLPARABEN MIXTURES

GROWTH (TGEA Subculture)
Preservatives (ppm, w/w)

| DAY | blank | SP 250 ppm | SP 500 ppm | MP 500 ppm | MP 1000 ppm | SP 250 ppm + MP 500 ppm | SP 500 ppm + MP 500 ppm | SP 250 ppm + MP 1000 ppm | SP 500 ppm + MP 1000 ppm |
|---|---|---|---|---|---|---|---|---|---|
| | | | | | Re-challenge | | | | |
| 72 | +++++ | +++++ | +++ | +++++ | +++++ | +++++ | + | +++ | − |
| 79 | +++++ | +++++ | +++++ | +++++ | +++++ | +++++ | +++ | +++++ | − |

What is claimed is:

1. An antimicrobial composition characterized by synergistic antibacterial and antifungal efficacy and comprising pyrithione acid or a pyrithione salt, or a combination thereof, and at least one compound selected from the group consisting of benzyl and lower alkyl esters of para-hydroxybenzoic acid, salts thereof, and combinations thereof.

2. The composition of claim 1 wherein said compound is a benzyl or lower alkyl ester of para-hydroxybenzoic acid, or a salt thereof, and the weight ratio of said compound to said pyrithione salt or pyrithione acid is between about 1:10 and about 10,000:1.

3. A method of imparting antimicrobial activity to a composition comprising water or an organic solvent which comprises adding thereto an antimicrobially effective amount of pyrithione acid or a pyrithione salt, or a combination thereof, and at least one compound selected from the group consisting of benzyl and lower alkyl esters of para-hydroxybenzoic acid, salts thereof, and combinations thereof.

4. The method of claim 3 wherein said compound is a benzyl or lower alkyl ester of para-hydroxybenzoic acid, or a salt thereof, and the weight ratio of said compound to said pyrithione salt is between about 1:1 and about 6,000:1.

5. A method of coating a substrate to provide an antimicrobially effective coating on the substrate which comprises contacting the substrate with a coating composition comprising pyrithione acid or a pyrithione salt, or a combination thereof, and at least one compound selected from the group consisting of benzyl and lower alkyl esters of para-hydroxybenzoic acid, salts thereof, and combinations thereof.

6. The method of claim 5 wherein said compound is a benzyl or lower alkyl ester of para-hydroxybenzoic acid, or a salt thereof, and the weight ratio of said compound to said pyrithione salt is between about 1:1 and about 6,000:1.

7. A coated substrate comprising a substrate together with a coating on said substrate, said coating being produced by:
   (a) contacting the substrate with a coating composition comprising pyrthione acid or a pyrithione salt, or a combination thereof, and at least one compound selected from the group consisting of benzyl and lower alkyl esters of para-hydroxybenzoic acid, salts thereof, and combinations thereof, to provide a coating on said substrate, and
   (b) drying said coating composition on said substrate to produce said coated substrate.

8. The coated substrate of claim 7 wherein said compound is a benzyl or lower alkyl ester of para-hydroxybenzoic acid, or a salt thereof, and the weight ratio of said compound to said pyrithione salt is between about 1:1 and about 6,000:1.

9. A paint comprising:
   (a) a base medium comprising water or a resin selected from the group consisting of vinyl, alkyd, epoxy, acrylic, polyurethane and polyester resins, and combinations thereof,
   (b) pyrithione acid or a pyrithione salt, or a combination thereof, and
   (c) a compound selected from the group consisting of benzyl and lower alkyl esters of para-hydroxybenzoic acid, salts thereof, and combinations thereof.

10. A soap, shampoo or skin care medicament comprising a suitable carrier, pyrithione acid or a pyrithione salt, or a combination thereof, and a compound selected from the group consisting of benzyl and lower alkyl esters of para-hydroxybenzoic acid, salts thereof, and combinations thereof.

11. A metalworking fluid containing water or an organic base fluid, a pyrithione, and a compound selected from the group consisting of benzyl and lower alkyl esters of para-hydroxybenzoic acid, salts thereof, and combinations thereof.

12. The metalworking fluid of claim 11 which additionally contains a component selected from the group consisting of corrosion inhibitors, surfactants, and combinations thereof.

13. A composition comprising a plastic or a woven or non-woven fiber which comprises, in combination, a plastic or a fiber and a compound selected from the group consisting of benzyl and lower alkyl esters of para-hydroxybenzoic acid, salts thereof, and combinations thereof.

* * * * *